United States Patent [19]

Nagasaki et al.

[11] Patent Number: 4,615,330
[45] Date of Patent: Oct. 7, 1986

[54] NOISE SUPPRESSOR FOR ELECTRONIC ENDOSCOPE

[75] Inventors: Tatsuo Nagasaki, Musashino; Hiroyoshi Fujimori, Hachioji, both of Japan

[73] Assignee: Olympus Optical Co., Ltd., Japan

[21] Appl. No.: 645,308

[22] Filed: Aug. 29, 1984

[30] Foreign Application Priority Data

Sep. 5, 1983 [JP] Japan ................... 58-163594
Sep. 5, 1983 [JP] Japan ................ 58-138207[U]

[51] Int. Cl.$^4$ ............................................ A61B 1/00
[52] U.S. Cl. ......................... 128/4; 128/660; 128/303.15; 174/102 R
[58] Field of Search ............... 128/303.13–303.17, 128/786, 4, 660, 6; 174/102 R; 333/241–243

[56] References Cited

U.S. PATENT DOCUMENTS

| 4,200,105 | 4/1980 | Gonser | 128/303.14 |
| 4,467,817 | 8/1984 | Harris | 128/786 |
| 4,487,489 | 12/1984 | Takamotsu | 128/303.15 |

FOREIGN PATENT DOCUMENTS

| 69528 | 4/1983 | Japan | 128/4 |
| 69530 | 4/1983 | Japan | 128/4 |
| 104505 | 6/1983 | Japan | 333/243 |

OTHER PUBLICATIONS

Hisanago, K. et al. "A New Trans-Digestive-Tract Scanner with a Gastro-Fiber-Scope", Proc. 23rd AIUM 1978 p. 188.

Primary Examiner—Kyle L. Howell
Assistant Examiner—Francis J. Jaworski
Attorney, Agent, or Firm—Ostrolenk, Faber, Gerb & Soffen

[57] ABSTRACT

A noise suppressor is provided for an electronic endoscope which incorporates a diathermic cutter or an ultrasonic diagnosis system. The electronic endoscope utilizes a solid-state camera, and in order to prevent noises from being superimposed upon the signal fed to an image display, a transmission line which transmits a high frequency current to the diathermic cutter or a transmission line which transmits an ultrasonic signal to or receives an ultrasonic signal from an ultrasonic probe is shielded by a conductor member. In particular, for a transmission line which conveys the high frequency current, impedance regulating means is connected therewith in order to prevent the high frequency current from leaking through a distributed capacitance between the transmission line and the conductor member. Alternatively, a narrow bandpass filter may be provided which limits the frequency band of the high frequency current. A coaxial cable may be used in which both the transmission line and the conductor member are formed of conductive rubber.

16 Claims, 8 Drawing Figures

NOISE SUPPRESSOR FOR ELECTRONIC ENDOSCOPE

BACKGROUND OF THE INVENTION

The invention relates to a noise suppressor for an electronic endoscope, and more particularly, to an apparatus which effectively suppresses noises from other instruments which may be either combined with or internally housed within an endoscope, for use with an electronic display which produces the image of an object being examined for observation in response to a video signal from a solid-state camera located within a portion of an endoscope that is adapted to be inserted into coeloma.

Recently, a rapid advance in the electronic technology has brought CCD (charge coupled device), BBD (bucket brigade device) or MOS (metal oxide semiconductor) sensors or similar solid-state camera elements into practical use, which are being increasingly utilized in electronic endoscope for observing an object being examined by an endoscope. (It is to be understood that the term "electronic endoscope" is intended to mean a combination of a mechanical endoscope of more or less common design with an associated electronic display which is used to produce an image of an affected part being observed by the endoscope.)

However, an endoscope which is provided with such electronic display may include a high frequency diathermic cutter or snare for diathermy by high frequency cautery or for sampling of a living body. In such cases, high frequency current from a power supply for diathermy may be superimposed as noise on a video signal which is obtained as a solid-state camera element is being scanned, thus causing the reproduced image on the image display to be blurred.

Figure 2:
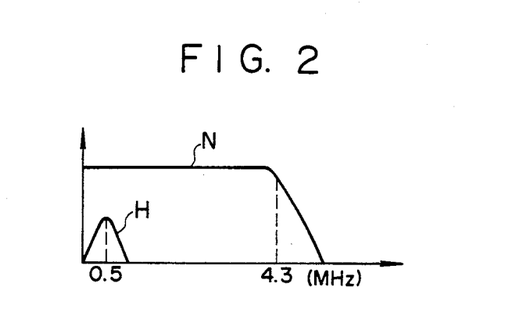
FIG. 2 graphically shows the relationship between the frequency spectrum of a video signal and the frequency spectrum of a high frequency current.

A high frequency current which is output from a power supply for diathermy has a frequency which is chosen above 300 kHz in order to avoid influences upon an object being examined such as human body. On the other hand, a video signal supplied to the electronic display has a frequency band of 4.3 MHz, for example, when a color picture is used. FIG. 2 graphically shows the relationship between the frequency spectrum N of a color video signal and the frequency spectrum H of a high frequency current, the spectral intensity being shown on the ordinate and the frequency being shown on the abscissa. It will be seen that the frequency spectrum H of the high frequency current has a center frequency of 0.5 MHz with a response extending to the opposite sides thereof. The spectrum H represents a band spectrum having a certain width rather than a single spectral line, which is considered to be caused by the fact that the high frequency oscillation within the power supply for diathermy includes components other than a fundamental wave, which are distorted during the amplification of a high frequency signal.

When the frequency band of the video signal for the electronic display overlaps the frequency band of a high frequency current supplied to the diathermic cutter, the electromagnetic induction between the lines which convey the video signal and the high frequency current causes the high frequency signal to be superimposed, as noise, upon the video signal, causing a blurring of an image which is reproduced on the display. In particular, when the diathermic cutter is passed through the endoscope to effect a surgical operation, the blurring of the image may prevent the object being examined from being properly recognized, and in the worst cases, require the surgical operation to be interrupted.

To eliminate such inconveniences of the prior art, noise suppressors for electronic endoscope have already been proposed (Japanese Laid-Open Patent Applications No. 69,528/1983 and No. 69,530/1983) in which a solid-state camera element and an amplifier circuit are shielded, together with a choice of the high frequency current in a frequency band which is higher than the frequency band of the video signal to avoid an interference therewith or in which the frequency band of the video signal is chosen higher than the frequency band of the high frequency current to avoid an interference therewith.

However, it will be noted that in these noise suppressors, the frequency band of either the high frequency current or the video signal must be changed, requiring a change in the specification for the power supply of diathermy or image reproducing apparatus and thus preventing the direct use of the existing power supply or image reproducing apparatus, which is inconvenient. In other words, the noise suppressor of the prior art cannot suppress the influences of a the high frequency current upon the video signal while at the same time allowing the frequency bands of the both signal components to overlap each other.

On the other hand, an endoscope is already available on the market which incorporates an ultrasonic diagnosis system having an ultrasonic probe disposed within the distal end of a portion of the endoscope which is adapted to be inserted into coeloma or having an ultrasonic mirror associated with a probe which is rotated for scanning, thus transmitting to or receiving from internal organs ultrasonic waves for depicting an acoustic picture information of such organs on an image display.

When the electronic display incorporating a solid-state camera is used in combination with such ultrasonic diagnosis system in an endoscope, the signal to or from the ultrasonic probe may be superimposed, as noise, on the video signal supplied to the electronic display, again causing a blurring of an image being reproduced.

It will be noted that a cable which transmits a signal to the ultrasonic probe or receives a signal therefrom is passed through a portion of an endoscope adapted to be inserted into coeloma from an operating end thereof for connection with the ultrasonic probe. This cable has a relatively large diameter because a high voltage on the order of several hundreds to one kilovolt peak-to-peak is supplied to the probe. If a standard cable comprising a copper wire clad with an insulating material, for example, is used, such cable does not have a sufficient durability in response to bending, and may disadvantageously cause a failure such as breakage when used in an endoscope which is subject to repeated flexure. Such inconvenience will be aggravated if the cable is shielded to suppress adverse influences upon the video signal, thereby increasing the cable diameter. Thus, there has been a need in the prior art for coaxial cable which has an increased bending resistance. The same is true with a transmission cable which supplies a high frequency current to a "Messer" located at the distal end of the endoscope when a diathermic cutter is to be used.

SUMMARY OF THE INVENTION

It is an object of the invention to provide a noise suppressor for electronic endoscope which positively suppresses the superimposition of a high frequency current upon a video signal in the form of noise so as to enable the reproduction of a faithful and sharp image where both the video signal and the high frequency current supplied to a diathermic cutter have overlapping frequency bands and which is also capable of efficiently supplying power to the "Messer" located at the distal end of the diathermic cutter.

It is another object of the invention to provide such noise suppressor which prevents a signal transmitted to or received from an ultrasonic probe from being superimposed as noise upon a video signal of the electronic display when the latter is used in combination with an ultrasonic diagnosis system.

It is a further object of the invention to provide a coaxial cable which provides a sufficient shielding effect when used to transmit a high frequency current or to transmit or receive an ultrasonic signal and which has an increased bending strength while enabling a flexure with a reduced radius of curvature, thus avoiding the likelihood of failure such as breakage when used in an endoscope which is subject to repeated flexure.

It is a feature of the invention to employ a transmission line which is shielded by a conductor member for conveying a high frequency current from a power supply for diathermy to a diathermic cutter, with impedance regulating means, formed as by a coil, interposed between the transmission line and the conductor member. The distributed capacitance between the transmission line and the conductor member and the inductance of the impedance regulating means form a parallel resonance circuit having a resonance frequency which is chosen to be coincident with the frequency of the high frequency current, thereby minimizing the power loss of the high frequency current which may be caused by the distributed capacitance.

It is another feature of the invention to employ a coaxial cable as a transmission line to transmit a signal to an ultrasonic probe or to receive a signal therefrom, thereby preventing the superimposition of such signal as noises upon a video signal supplied to an electronic display.

It is a further feature of the invention to form a coaxial cable by means of conductive rubber which is used as a transmission line and as a shielding conductor member, thus imparting to the cable an increased bending resistance.

According to the invention, a transmission line for a high frequency current which is fed from a power supply for diathermy to a diathermic cutter is shielded by a conductor member, and impedance regulating means is interposed between the transmission line and the conductor member to prevent the high frequency current from being superimposed upon a video signal fed to an electronic display. This also minimizes the power loss of the high frequency current which may be caused by the distributed capacitance between the transmission line and the conductor member, thus enabling an efficient transmission of the high frequency current to the "Messer" located at the distal end of the diathermic cutter.

Also in accordance with the invention, a transmission line which conveys a signal transmitted to or received from an ultrasonic probe is defined by a coaxial cable, again effectively preventing such signal from being superimposed upon the video signal as noises.

The use of conductive rubber as the transmission line and the shielding conductor member according to the invention achieves an increased bending resistance.

DESCRIPTION OF PREFERRED EMBODIMENTS

Figure 1:
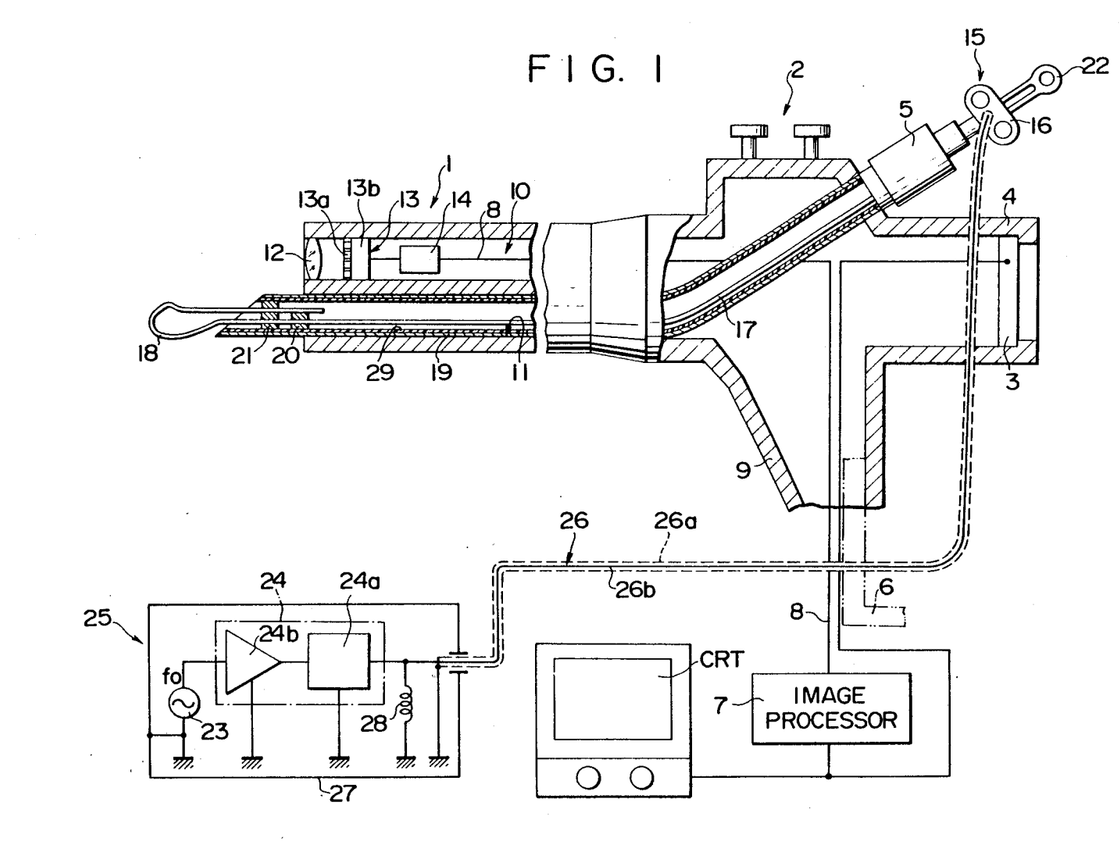
FIG. 1 is a schematic view of a noise suppressor for electronic endoscope according to one embodiment of the invention.

Referring to FIG. 1, there is shown an endoscope including a portion 1 which is adapted to be inserted into coeloma and which extends from an operating end 2. The operating end 2 includes an eyepiece assembly 4 which may be integrally formed therein or may be detachably mounted thereon, the assembly 4 having a display 3 comprising a liquid crystal panel. The operating end 2 also includes a station 5 for inserting a treatment tool, and an outlet 9 for passing a light guide cable 6 and signal leads 8 extending to an image processor circuit 7 or the like.

The image processor circuit 7 is connected to an image display which may, for example, comprise a cathode ray tube CRT allowing an image of an internal organ to be displayed on the display CRT in response to a video signal which may be supplied through the signal lead 8. The circuit 7 also generates a supply voltage which is fed to a preamplifier 14 to be described later. An output from the image processor circuit 7 is also fed to the liquid crystal panel 3 so that the same image as displayed by the image display CRT can be observed on the eyepiece assembly 4 simultaneously. It is also possible to enable the image display CRT alone without activating the liquid crystal panel 3.

It is to be understood that the inserted portion 1 of the endoscope is formed with a variety of channels including a signal channel 10 through which the signal leads 8 extend, a treatment tool channel 11 and a light guide channel, not shown, through which the cable 6 extends. An objective lens 12 is fitted into an opening of the signal channel 10 which is located at the distal end of the inserted portion 1, and a solid-state camera 13 which may comprise a charge coupled device (CCD), for example, is disposed rearwardly of the lens 12. The camera 13 includes a photoelectric converter 13a and a storage/read-out unit 13b. The objective lens 12 focusses an image of an object being examined upon the photoelectric transducer 13a, which then converts the image photoelectrically to supply an electric charge to the storage/read-out unit 13b for storage therein. Subsequently, such charge is read out line-by-line in a sequential manner to provide a video signal, which is then applied to the preamplifier 14. After amplification by the preamplifier 14, the output signal is delivered to the signal lead 8.

A diathermic cutter 15 may be introduced through the station 5 so as to extend through the treatment tool channel 11 of the endoscope. The diathermic cutter 15 comprises a proximate end 16, a high frequency transmission line 17 and a distal end Messer 18 which is formed by folding the free end of the transmission line 17 into a loop. The transmission line 17 extends through an insulating, flexible sheath 19, which is externally coated with a shielding conductor member 29. The conductor member 29 is adapted to be flexed as the flexible sheath 19 is flexed, and to this end, is formed of a meshwork of metal wires, for example. When mounting, the diathermic cutter 15 is inserted into the free end of the sheath 19 and passed therethrough to reach the station 5. The attachment is completed when the distal end of the sheath 19 projects from the free end of the inserted portion 1 of the endoscope. It will be noted that the distal end Messer 18 projects beyond an opening formed in the free end of the sheath 19. As will be noted, a stop 21 is fixedly mounted within the sheath 19 adjacent to the free end thereof, and a slider 20 is slidably disposed within the sheath 19 at a location rearward of the stop 21. Both the slider 20 and the stop 21 are perforated to allow the high frequency transmission line 17 to pass therethrough, with the free end of the distal end Messer 18 being fixedly connected to the stop 21. The slider 20 may be moved within the sheath 19 by operating a knob 22, which is disposed within the proximate end 16 of the diathermic cutter 15. The loop which defines the distal end Messer 18 will be at its maximum diameter when the slider 20 moves into abutment against the stop 21. An affected portion of an object being examined may be engaged with the loop, and then the knob 22 may be pulled toward a user, thereby retracting the slider 20 to reduce the diameter of the loop to allow the Messer 18 to hold the affected part.

The diathermic cutter 15 is connected through a high frequency transmission cable 26 to a power supply 25 for diathermy which produces a high frequency current for driving the cutter 15. The power supply 25 essentially comprises a source of high frequency signal 23 which oscillates at high frequency $f_0$, and a power amplifier 24 for amplifying the high frequency signal from the source 23 to deliver a high frequency current. The source 23 has its one end connected to the ground and its other end connected to the input terminal of a power amplifier section 24b of the power amplifier 24. The amplifier section 24b has an output terminal which is connected through a narrow bandpass filter 24a to one end of a transmission line 26b of the high frequency transmission cable 26. The amplifier section 24b may comprise a push-pull amplifier circuit, for example, while the filter 24a may comprise an LC circuit. It will be noted that both the amplifier section 24b and the filter 24a are connected to the ground within the power supply 25 as is one end of a shielding conductor member 26a of the cable 26. In addition, the power supply 25 is shielded within a conductive casing 27 which is also connected to the ground. A coil 28 is connected between the output of the filter 24a and the ground to provide impedance regulating means as will be described later.

The high frequency transmission cable 26 may comprise a coaxial cable, for example, and the other end of the transmission line 26b is connected to the high frequency transmission line 17 within the proximate end 16 of the diathermic cutter 15. The other end of the shielding conductor member 26a is connected to the shielding conductor member 29 within the proximate end 16 also (see FIG. 3). The coil 28 disposed within the power supply 25 has a magnitude of inductance L which is chosen such that the resonance frequency of a parallel resonance circuit defined by the inductance L and the distributed capacitance C between the transmission lines 17, 26b and the shielding conductor members 29, 26a coincides with the frequency $f_0$ of the power supply 25. The high frequency current which is fed from the power supply 25 to the distal end Messer 18 through the transmission lines 26b, 17 returns to the ground of the power supply 25 through an object (person) being examined and a grounding plate, not shown, which is attached to the object being examined.

Figure 3:
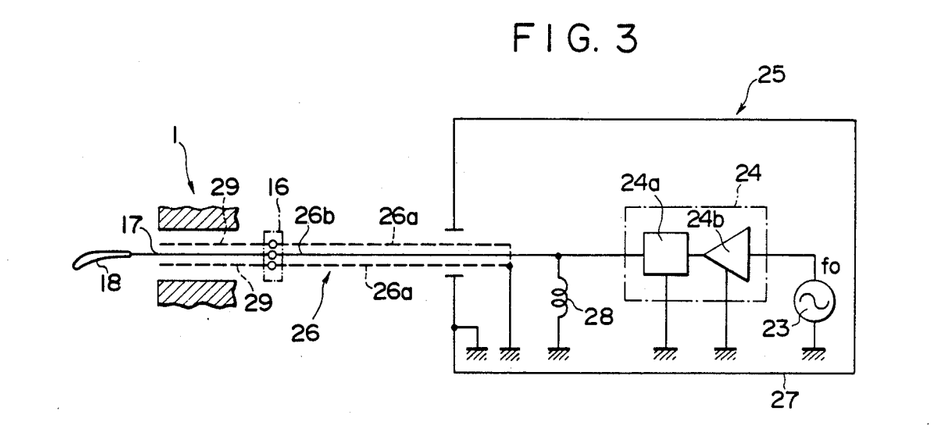
FIG. 3 is a schematic diagram illustrating the fundamental arrangement of the noise suppressor shown in FIG. 1.
Figure 4:
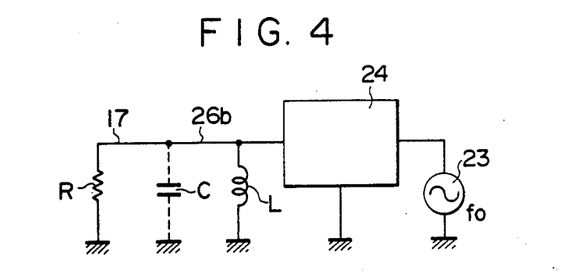
FIG. 4 is an equivalent circuit of the arrangement shown in FIG. 3.

FIG. 3 shows the fundamental arrangement of the noise suppressor constructed in the manner mentioned above, and its equivalent circuit is illustrated in FIG. 4. In FIG. 4, a resistor R represents a discharge resistor component between the Messer 18 and the grounding plate attached to the object being examined, capacitor C the distributed capacitance between the transmission lines 26b, 17 and the shielding conductor members 26a, 29, and inductance L the inductance of the impedance regulating coil 28.

In operation, the high frequency current having the center frequency $f_0$ which is produced by the source 23 is power amplified by the power amplifier section 24b. The amplified current has a spectral distribution including frequency components other than the center frequency $f_0$ of 0.5 MHz, for example, which are distributed on the opposite sides of the center frequency (see FIG. 2). The amplified high frequency current is passed through the narrow bandpass filter 24a to limit it to a narrow band. The high frequency current is then fed through the transmission line 26b of the transmission cable 26 and the transmission line 17 of the diathermic cutter 15 to the distal end Messer 18, and then passes to the grounding plate through the object being examined.

It will be understood that there is a possibility that the high frequency current may leak through the distributed capacitance C between the transmission lines 26b, 17 and the shielding conductor members 26a, 29. In accordance with the invention, such leakage of the high frequency current around the object being examined is minimized by the provision of the coil 28 having the inductance L which forms a parallel resonance circuit tuned to the center frequency $f_0$ of the high frequency current together with the distributed capacitance C. In this manner, the impedance across the transmission lines 26b, 17 and the shielding conductors 26a, 29 is increased to suppress the leakage of the high frequency current through the distributed capacitance C, thus allowing the high frequency current to be delivered to the distal end Messer in an efficient manner. Specifically, by choosing the inductance L of the coil 28 such that $$f_0 = \frac{1}{2\pi \sqrt{LC}}$$

the loss of the high frequency current through the distributed capacitance is minimized.

With the above arrangement, no high frequency current can be induced upon the signal leads 8 conveying the video signal since the transmission lines 26b, 17 conveying the high frequency current are shielded by the conductor members 26a, 29, thus assuring that a sharp image be produced on the image display CRT which is free from noises.

The coil 28 is effective to suppress the loss of the high frequency current through the distributed capacitance C between the transmission lines 26b, 17 and the shielding conductor members 26a, 29, contributing to an efficient delivery of the high frequency current to the distal end Messer 18.

In addition, since the sheath 19 is surrounded by the shielding conductor member 29, there is an advantage that a conventional diathermic cutter may be used by simply changing the sheath therefor.

It will be seen that the invention resides in shielding the high frequency transmission lines 26b, 17 and minimizing the power loss of high frequency current which may leak through the distributed capacitance between these transmission lines 26b, 17 and the shielding conductor members 26a, 29 by the provision of the impedance regulating means. It is to be noted that in certain instances, the provision of the impedance regulating means alone may be sufficient to allow the narrow bandpass filter 24a to be dispensed with.

The high frequency current is shielded from the video signal in that provision is made to prevent the high frequency current from disturbing clock pulses which are generated within the image processor circuit 7 for driving the solid-state camera or from interfering with the operation of the photoelectric converter 13a to influence upon the magnitude of charge that is stored in the storage/read-out unit 13b.

Figure 5:
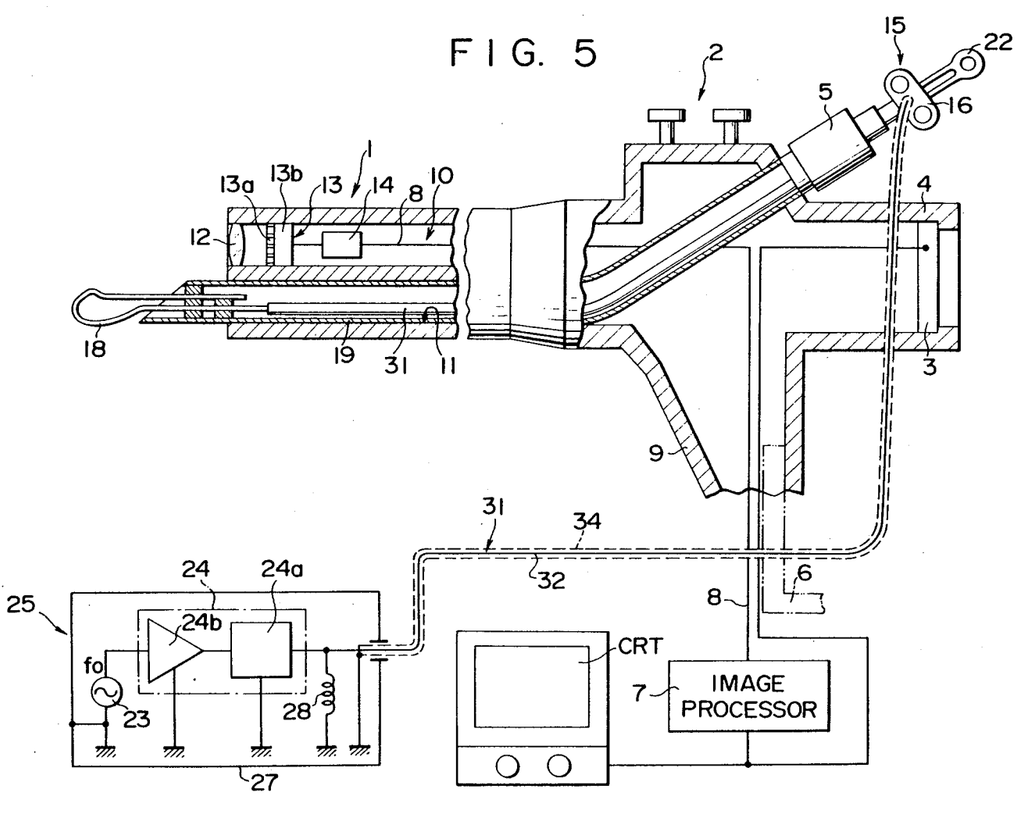
FIG. 5 is a schematic view of a noise suppressor according to another embodiment of the invention.

FIG. 5 shows another embodiment of noise suppressor for electronic endoscope. In this embodiment, the high frequency transmission lines 26b, 17 and the shielding conductor members 26a, 29 of the embodiment shown in FIG. 1 are replaced by a one-piece coaxial cable 31. Accordingly, corresponding parts are designated by like reference characters without repeating their description.

Figure 6:
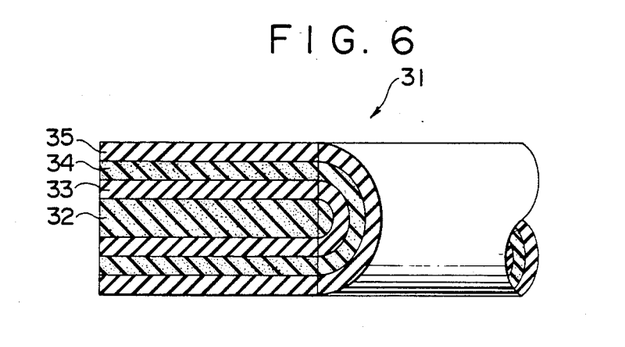
FIG. 6 is a side elevation, partly in section, of a coaxial cable used in the noise suppressor of FIG. 5.

As shown in FIG. 6, the coaxial cable 31 comprises a transmission line 32 formed of conductive rubber, an insulating layer 33 formed of a flexible material such as synthetic resin or rubber and disposed in surrounding relationship with the transmission line 32, a shielding conductor member 34 formed of conductive rubber and disposed in coaxial relationship with the transmission line 32 and in surrounding relationship with the insulating layer 33, and an insulating skin layer 35 formed of a flexible material such as synthetic resin or rubber and disposed in surrounding relationship with the conductor member 34. Consequently, the entire coaxial cable 31 has a good flexibility, and is capable of withstanding repeated flexure. In addition, the cable 31 can be restored from bending into a small radius of curvature.

The distal end Messer 18 comprises a metal wire in the similar manner as shown in the embodiment of FIG. 1, and is attached to the free end of the coaxial cable 31 in electrical connection with the transmission line 32 thereof.

The noise suppressor of the present embodiment achieves the similar functioning and effectiveness as those achieved with the embodiment of FIG. 1. Additionally, the full flexibility and restorability of the coaxial cable 31 avoids the likelihood of a failure such as breakage of the transmission line when the endoscope is subject to repeated flexure.

Figure 7:
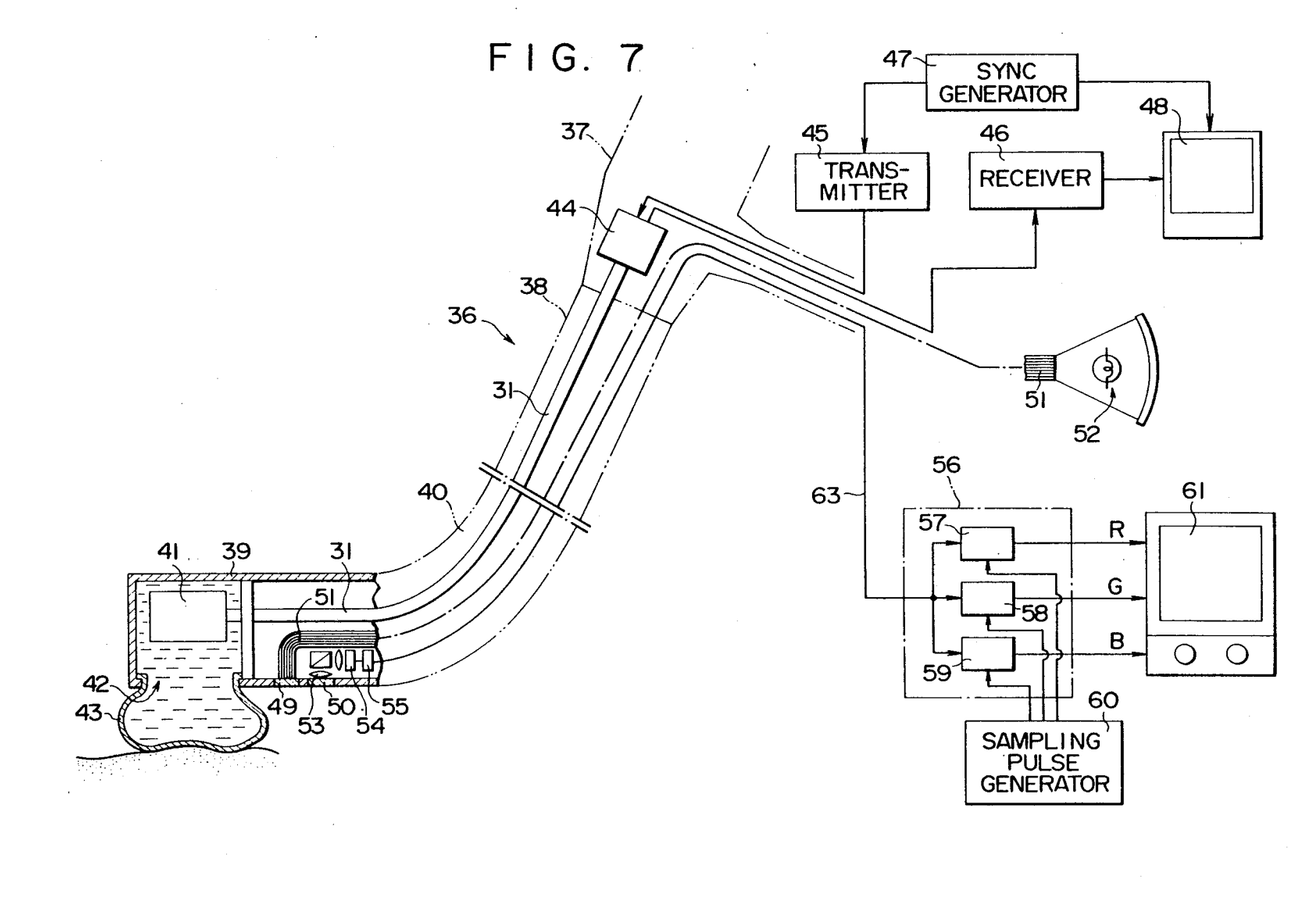
FIG. 7 is a schematic view of a noise suppressor according to a further embodiment of the invention.

FIG. 7 shows a further embodiment of noise suppressor for electronic endoscope which incorporates an ultrasonic diagnosis system. Specifically, an endoscope 36 includes a proximate operating end 37 which also serves as a handle. It also comprises an elongate, flexible inserted portion 38 which extends from the operating end 37. The inserted portion 38 includes a distal end 39 which is contiguously connected with a flexing portion 40 which can be operated by flex means, as by pulling or release of wires, not shown, so as to direct the distal end 39 to the left or right or up and down. An ultrasonic probe 41 is received within the distal end 39, in the side of which is formed a window 42 for transmitting or receiving ultrasonic wave. A balloon containing an ultrasonic wave transmitting liquid medium is attached to the window 42. The operating end 37 houses a motor 44, the drive shaft of which is connected to one end of the coaxial cable 31 shown in FIG. 6, with the other end of the cable 31 being connected to the probe 41 after passing through the inserted portion 38, thus allowing the probe 41 to be rotated for scanning purpose. The transmission line 32 and the shielding conductor member 34 of the coaxial cable 31 are electrically connected to the probe 41, which is in turn connected through the coaxial cable 31 and the motor 44 to a transmitter 45 and a receiver 46. The transmitter 45 is connected to a sync signal generator 47 while the receiver 46 is connected to a display or cathode ray tube 48 which is in turn connected to the sync signal generator 47. In this manner, the coaxial cable 31 is employed as rotation transmitting means which transmits the rotation from the motor 44 to the probe 41, and is also employed as signal transmitting means which supplies a pulse signal from the transmitter 45 to the probe 41 for generating an ultrasonic wave and which supplies an electrical signal, to which an ultrasonic echo is converted by the probe 41, to the receiver 46.

An illumination window 49 and an observation window 50 are formed in the same side of the distal end 39 as that in which the window 42 is formed, but are offset slightly rearward thereof. A light guide 51 comprising a bundle of optical fibers, for example, has its one end disposed in opposing relationship with the illumination window 49 for projecting illuminating light from a light source 52 through the illumination window 49, thus illuminating the object being examined. An objective lens 53 is disposed in opposing relationship with the observation window 50, and a solid-state camera 54 is disposed rearward of the objective lens 53. To enable a color photography, the camera 54 includes a color mosaic filter or color stripe filter. Light reflected by the object being examined passes through the objective lens 53 and impinges upon the solid-state camera 54 as light comprising three colors of red (R), green (G) and blue (B) formed by the color mosaic or color stripe filter. A driver and preamplifier circuit 55 which drives the camera 54 and amplifies an output therefrom is used to convert an output from the camera into a corresponding electrical signal, which is then fed through a signal lead 63 to a signal processor circuit 56. The signal processor circuit 56 essentially comprises three sample-and-hold circuits 57, 58 and 59 for R, G and B components, respectively. A sampling pulse generator 60 produces sampling pulses corresponding to the color mosaics or color stripes to sample the electrical signal for each of R, G and B components for output to a color cathode ray tube 61. In this manner, the sample-and-hold circuits 57, 58 and 59 output R, G and B signals to provide a color display on the cathode ray tube 61.

While the use of a color camera including a color mosaic filter or a color stripe filter has been disclosed to provide means which produces a color display in the present embodiment, it should be understood that a normal black-and-white camera without any color filter may be used in combination with a light source which sequentially switches between three colors of light for illumination, thus providing color display means.

Where the solid-state camera 54 is employed as observation means of the endoscope 36, the transmission line 32 is electrically shielded by the conductor member 34 of the coaxial cable 31 in order to prevent the signal to or from the probe 41 from being superimposed upon the electrical signal from the solid-state camera 54 as noises.

With the described arrangement, the endoscope 36 may be used in a manner such that light for illumination is projected through the illumination window 49, and light reflected from the coeloma is admitted through the observation window 50 to impinge upon the solid-state camera 54 such as may be formed with CCD elements to convert the image into a corresponding electrical signal, which is used to display an image of the object on the cathode ray tube 61. Accordingly, while observing the image of the object being examined on the display, the inserted portion 38 may be inserted into the coeloma and the distal end 39 including the illumination window 49, observation window 50 and ultrasonic probe 41 may be directed in any direction desired by operating the flexing portion 40, thus bringing the balloon 43 attached to the window 42 into abutment against any desired organ. Subsequently, the motor 44 and the coaxial cable 31 may be utilized to rotate the probe 41 for scanning while simultaneously supplying a pulse signal to the probe 41 by means of the transmitter 45, motor 44 and coaxial cable 31 so as to cause the probe 41 to transmit the ultrasonic wave toward the organ through the balloon 43 which contains ultrasonic wave transmitting liquid medium. A reflected echo is converted into an electrical signal by the probe 41, and this signal is fed through the coaxial cable 31 and motor 44 to be input to the receiver 46 where the electrical signal is amplified and detected to provide a display of ultrasonic tomographic image on the cathode ray tube 48 in response to a sweep signal which is synchronized with a sector scanning.

As mentioned previously, in this embodiment, the coaxial cable 31 is utilized to transmit rotation to the ultrasonic probe 41, and also to transmit the signal to or from the probe 41. Nevertheless, no breakage of the coaxial cable 31 occurs if it is repeatedly folded or rotated by a flexure of the flexing portion 40. The voltage applied to the probe 41 is as high as several hundred volts to one kilovolt peak-to-peak, and hence, if a usual cable is used, the pulse signal applied to the probe 41 will be superimposed as noises upon the electrical signal from the camera 54. However, the use of the coaxial cable 31 to transmit a signal to or to receive a signal from the probe 41 allows such signal to be electrically shielded and prevented from being superimposed upon the electrical signal from the solid-state camera 54 as noises.

While the described embodiment is of a type in which the probe is rotated and accordingly the coaxial cable 31 is used as means to transmit the rotation to the probe, it will be appreciated that in an arrangement in which the probe does not rotate, but a scan mirror is driven for rotation, a different member may be used to transmit the rotation to such scan mirror while using the coaxial cable 31 simply as means which transmits a signal to or receives a signal from the probe. The endoscope 36 shown in FIG. 7 is of a lateral view type, but any other endoscope such as a direct view or an oblique view type may be used as desired.

Figure 8:
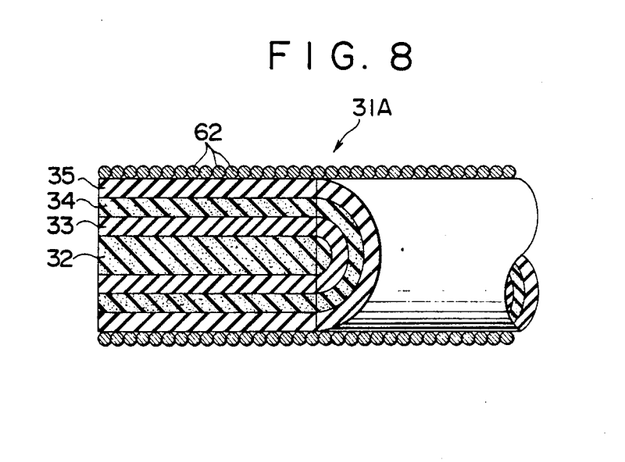
FIG. 8 is a side elevation, partly in section, of a modification of the coaxial cable shown in FIG. 6.

FIG. 8 shows a modification of the coaxial cable 31 shown in FIG. 6. In this modification, a coaxial cable 31A additionally comprises a close pitch coil 62 which surrounds the insulating skin layer 35 of the coaxial cable 31 mentioned above. This construction increases the rigidity of the coaxial cable 31A, allowing an improvement in its functioning as means which transmits the rotation. Accordingly, such cable is preferred for use in the arrangement of FIG. 7 in order to transmit the rotation to the ultrasonic probe 41.

What is claimed is:

1. A combination, comprising:
   (A) an endoscope having an insertable portion adaptable to be inserted into a coeloma, said endoscope including:
      (1) a solid-state camera disposed within said insertable portion for converting an image of an object being examined into a video signal; and
      (2) a video signal lead extending through the insertable portion for conveying the video signal output from the solid-state camera to an image processor, the video signal generated by the solid state camera and transmitted over the video signal lead falling within a first frequency spectrum;
   (B) a diathermic cutter removably insertable into a treatment tool channel of the endoscope and including:
      (1) a distal end Messer which effects excision of an object being examined through the endoscope in response to the application of a high frequency current thereto;
      (2) a transmission line extending through the diathermic cutter to transmit a high frequency current from a power supply for diathermy to the distal end Messer, the high frequency current having a second frequency spectrum which overlaps the first frequency spectrum; and
      (3) a conductor member which electrically shields the transmission line from the video signal lead.

2. A combination according to claim 1, further including impedance regulating means which establishes a high impedance between the conductor member and the transmission line with respect to a frequency band of the high frequency current.

3. A combination according to claim 2 in which the impedance regulating means comprises a coil connected to form a parallel resonance circuit together with a distributed capacitance between the transmission line and the conductor member at a frequency of the high frequency current.

4. A combination according to claim 2, in which the power supply for diathermy includes a narrow bandpass filter for limiting the frequency band of the high frequency current to a narrow band.

5. A combination according to claim 1 in which the conductor member is disposed in surrounding relationship with a sheath through which the diathermic cutter extends.

6. A combination according to claim 1 in which the transmission line and the conductor member are formed by a transmission line and a shielding conductor member of a coaxial cable.

7. A combination according to claim 6 in which the coaxial cable comprises a transmission line formed of conductive rubber, a flexible, insulating layer disposed in surrounding relationship with the transmission line, a conductor member formed of conductive rubber and disposed in surrounding relationship with the insulating layer, and a flexible, insulating skin layer disposed in surrounding relationship with the conductor member.

8. A coaxial cable comprising
a transmission line formed of conductive rubber;
a flexible, insulating layer disposed in surrounding relationship with the transmission line;
a shielding conductor member formed of conductive rubber and disposed in surrounding relationship with the insulating layer;
and a flexible, insulating skin layer disposed in surrounding relationship with the conductor member.

9. A coaxial cable according to claim 8, further including a close pitch coil disposed in surrounding relationship with the insulating skin layer.

10. A combination, comprising:
(A) an endoscope having an insertable portion adapted to be insertable into a coeloma, said endoscope including:
  (1) a solid-state camera disposed within the insertable portion for converting an image of an object being examined into a video signal; and
  (2) a video signal lead extending through the insertable portion for conveying the video signal output from the solid-state camera to an image processor;
(B) a diathermic cutter which is removably insertable into a treatment tool channel of the endoscope and including:
  (1) a distal end Messer which effects excision of an object being examined through the endoscope in response to the application of a high frequency current thereto;
  (2) a transmission line extending through the insertable portion to transmit a high frequency current from a power supply for diathermy to the distal end Messer;
  (3) a conductor member which electrically shields the transmission line from the video signal leads; and
  (4) impedance regulating means which establishes a high impedance between the conductor member and the transmission line with respect to a frequency band of the high frequency current, the impedance regulating means comprising a coil connected to form a parallel resonant circuit together with a distributed capacitance between the transmission lines and the conductor member at a frequency of the high frequency current.

11. An electronic endoscope, comprising:
(A) an endoscope having an insertable portion adapted to be insertable into a coeloma, said endoscope including:
  (1) a solid-state camera disposed within the insertable portion for converting an image of an object being examined into a video signal;
  (2) a video signal lead extending through the insertable portion for conveying the video signal output form the solid-state camera to an image processor;
(B) a diathermic cutter removably insertable into a treatment tool channel of the endoscope and including:
  (1) a distal end Messer which effects excision of an object being examined through the endoscope in response to the application to a high frequency current thereto;
  (2) a transmission line extending through the diathermic cutter to transmit a high frequency current from a power supply for diathermy to the distal end Messr; and
  (3) a conductor member which electrically shields the transmission line from the video signal lead, the conductor member being disposed in surrounding relationship with a sheet through which the diathermic cutter extends.

12. A combination, comprising:
(A) an endoscope having an insertable portion adapted to be insertable into a coeloma, said endoscope including:
  (1) a solid-state camera disposed within the insertable portion for converting an image of an object being examined into a video signal; and
  (2) a video signal lead extending through the insertable portion for conveying the video signal output from the solid-state camera to an image processor;
(B) a diathermic cutter removably insertable into a treatment tool channel of the endoscope and including:
  (1) a distal end Messer which effects excision of an object being examined through the endoscope in response to the application of a high frequency current thereto;
  (2) a transmission line extending through the insertable portion to transmit a high frequency current from a power supply for diathermy to the distal end Messer; and
  (3) a conductor member which electrically shields the transmission line from the video signal lead, the transmission line and the conductive member being formed by a transmission line and a shielding conductor member of a coaxial cable, respectively.

13. A combination according to claim 12 in which the coaxial cable comprises a transmission line formed of a conductive rubber, a flexible, insulating layer disposed in surrounding relationship with the tramsmission line, a conductor member formed of a conductive rubber and disposed in surrounding relationship with the insulating layer and a flexible, insulating skin layer disposed in surrounding relationship with the conductor member.

14. An electronic endoscope, comprising:
an insertable portion adapted to be inserted into a coeloma;
a solid-state camera disposed with the insertable portion for converting an image of an object being examined into a video signal;
a video signal lead extending through the insertable portion for conveying the video signal output from the solid-state camera to an image processor; and
an ultrasonic probe disposed within the insertable portion for transmitting an ultrasonic wave toward an object being examined and for receiving a reflected wave therefrom;
a transmission line extending through the insertable portion for transmitting an activating signal to the ultrasonic probe and the reflected signal from the probe to an ultrasonic diagnosis system; and
a conductor member for electrically shielding the transmission line from the video signal lead, the transmission line and the conductor member being formed by a transmission line and a shielding conductor member of a coaxial cable, respectively, the coaxial cable comprising the transmission line formed of a conductive rubber, a flexible, insulating layer disposed in surrounding relationship with the transmission line, a conductor member formed of a conductive rubber and disposed in surrounding relationship with the insulating layer, and a flexible, insulating skin layer disposed in surrounding relationship with the conductor member.

15. An endoscope according to claim 14 in which the coaxial cable further comprises a close pitch coil disposed around the insulating skin layer.

16. An endoscope according to claim 14 in which the coaxial cable also serves as means for transmitting a scanning motion to the ultrasonic probe.

* * * * *